Figure 2:
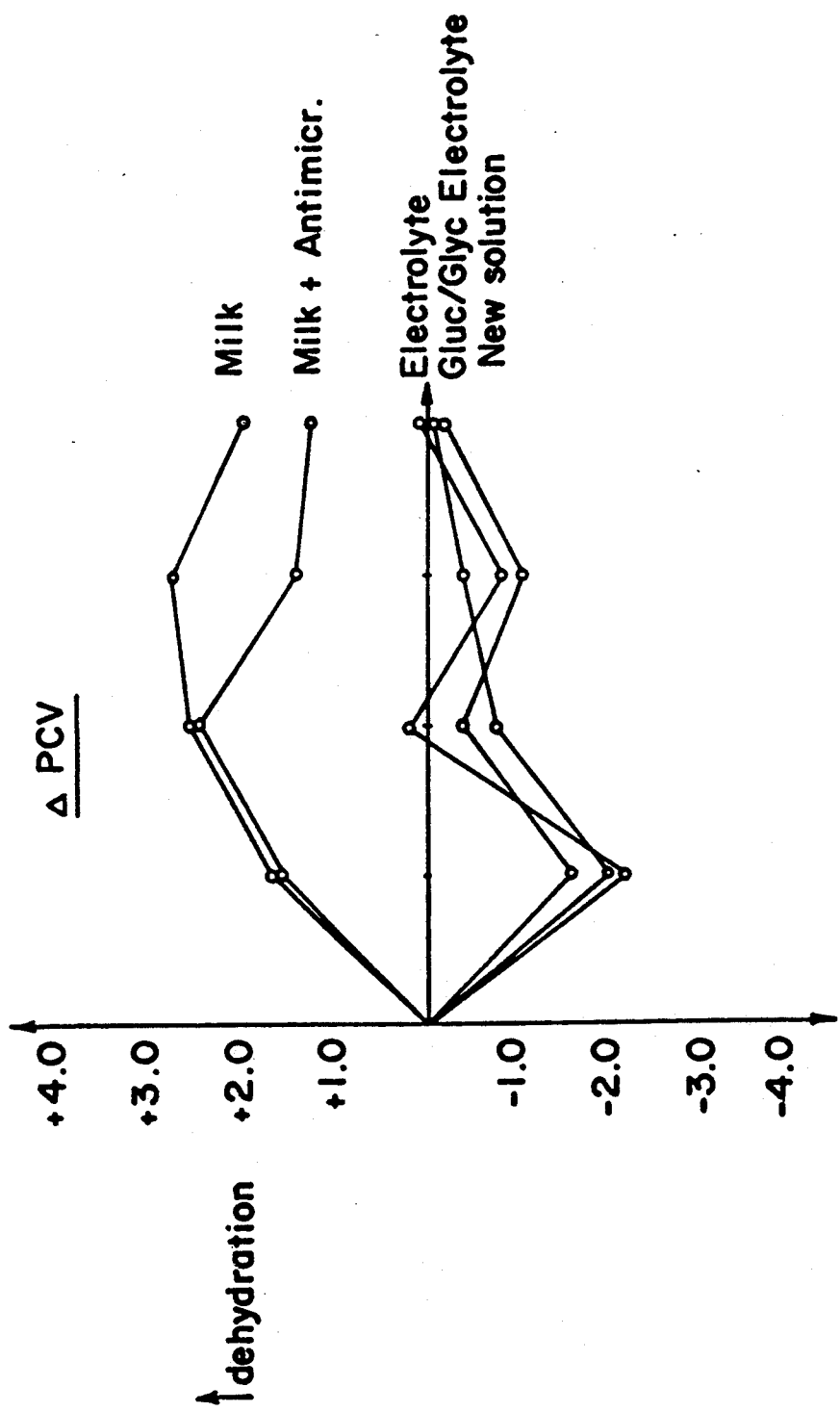

United States Patent [19]

Jerrett

[11] Patent Number: 5,028,437

[45] Date of Patent: Jul. 2, 1991

[54] TREATMENT OF ANIMAL DIARRHOEA

[75] Inventor: Ian V. Jerrett, Bairnsdale, Australia

[73] Assignee: The State of Victoria, Victoria, Australia

[21] Appl. No.: 396,053

[22] Filed: Aug. 21, 1989

Related U.S. Application Data

[63] Continuation-in-part of Ser. No. 86,260, Aug. 11, 1987, abandoned, which is a continuation of Ser. No. 760,744, filed as PCT AU84/00188 on Sep. 28, 1984, abandoned.

[30] Foreign Application Priority Data

Oct. 7, 1983 [AU] Australia .............................. PG1747

[51] Int. Cl.$^5$ ..................... A61K 35/20; A61K 33/10; A61K 33/13; A61K 31/70
[52] U.S. Cl. .................................... 424/535; 514/23; 514/557; 514/867; 424/677; 424/678; 424/679; 424/680; 424/681; 424/717
[58] Field of Search .............................. 424/677–681, 424/717, 95, 535; 514/23, 868, 557

[56] References Cited

U.S. PATENT DOCUMENTS 3,898,328 8/1975 Beigler et al. ...................... 424/153
4,322,407 3/1982 Ko ....................................... 424/128

OTHER PUBLICATIONS

The Veterinary Drug Encyclopedia, "Arnolyte" p. 12 (1964).
Swiss 242,335, cited in Chem. Abstracts vol. 43:6757i, (1949).

*Primary Examiner*—Jacqueline Stone
*Attorney, Agent, or Firm*—Birch, Stewart, Kolasch & Birch

[57] ABSTRACT

A veterinary composition useful for treatment of energy depletion, dehydration and electrolyte imbalance in diarrhoeic neonatal animals consisting essentially of
(a) glucose in an amount sufficient to produce a concentration level of from greater than 200 nM to 250 mM when in an aqueous solution,
(b) one or more sodium salts in an amount sufficient to produce a sodium ion concentration level of from 60 mM to 120 mM when in an aqueous solution, and
(c) one or more chloride salts in an amount sufficient to produce a chloride ion concentration level of 50 mM to 90 mM when in an aqueous solution.

15 Claims, 7 Drawing Sheets

CALF SCOUR TREATMENT

| Composition (mM) | Electrolyte | Gluc/Glyc Electrolyte | W.H.O. Recommendation | New Solution |
|---|---|---|---|---|
| Glucose | - | 111 | 110 | 227 |
| Glycine | - | 41 | - | - |
| Na⁺ | 50 | 74 | 90 | 86 |
| Cl⁻ | 48 | 74 | 80 | 86 |
| HCO₃⁻ | 24 | - | 30 | - |
| K⁺ | 43 | 17 | 25 | - |
| PO₄⁻ | 9 | 17 | - | - |
| Citric Acid | - | 1 | - | - |
| Osomolality | 174 | 335 | 335 | 399 |

FIG. 1

Calf Scour Trials 2 and 3 -- Moribund calves

| | Milk | Milk + Antimicr. | Electrolyte (trolyte) | Nutr/Elect (Vytrate) | New Soln. | |
|---|---|---|---|---|---|---|
| No. moribund calves | 1/12 | 5/12 | 2/11 | 2/11 | 0/12 | |
| Blood pH (norm. 7.40) | 7.15 | 6.92 | 7.19 | 6.82 | - | acidosis |
| Blood urea (mM) | 28.4 | 25.8 | 16.6 | 19.4 | - | dehydration |
| Glucose (normal 2.8 - 7.5 mM) | 1.5 | 7.3 | 0.5 | 0.3 | - | hypoglycaemia |

FIG. 4

TREATMENT OF ANIMAL DIARRHOEA

This application is a continuation-in-part application of U.S. patent application Ser. No. 07/086,260, filed Aug. 11, 1987, now abandoned, which was a continuation application of U.S. patent application Ser. No. 760,744, filed as PCT AU84/00188 on Sep. 28, 1984, now abandoned.

The present invention relates to a method of treatment of animal diarrhoea and for veterinary composition useful therefor.

Acute diarrhoeal diseases in animals particularly neonatal calves are amongst the most important causes of morbidity and mortality. Diarrhoea results in the loss from the animal of large quantities of water rich in bicarbonate, sodium, chloride and potassium. The animal thus becomes dehydrated, and the blood becomes more acidic. Continued feeding of milk to diarrhoeic neonatal animals may worsen the diarrhoea.

It is known that certain substances such as glucose, galactose and some amino acids (e.g. glycine) are actively absorbed from the intestine into the bloodstream and that simultaneous enhancement of water absorption occurs with the uptake of these substances. Glucose is the most readily available of these substances. Accordingly it is known in the prior art to stop feeding milk to calves suffering from diarrhoea and treat them with solutions containing glucose at a concentration required for sufficient water absorption (110–160 mM glucose). It is also known that sodium ($Na^+$) and chloride ($Cl^-$) are required for maximum absorption of glucose and water across epithelial cells. Accordingly it is also known to treat animal diarrhoea with electrolytes to increase water absorption and to replace losses of these substances in the faeces.

Rotavirus and cryptosporidia which cause direct epithelial damage and result in malabsorption diarrhoea are the most common causes of calf diarrhoea worldwide. In these infections malnutrition is as much, if not more of a consideration than dehydration. Moreover, energy requirements of neonatal calves kept outdoors in winter or spring are likely to be high. Other species such as pigs are highly susceptible to death from reduced energy intake in the neonatal period when diarrhoea is common. Recent investigations have shown that prior treatments for neonatal diarrhoea may lead to animals becoming severely hypoglycaemic and moribund.

It is accordingly an object of the present invention to overcome or at least alleviate, some of the difficulties and deficiencies related to the prior art.

The present invention thus relates to the use of the glucose/sodium/water intestinal transport system. The invention describes the use of concentration ranges of glucose, sodium and chloride to provide for adequate energy intake while maintaining effective rehydration properties. The present invention will now be more fully described with reference to cattle particularly neonatal calves. It should be understood however that whilst the present invention is of particular advantage in the treatment of such animals it is in no way restricted thereto.

Accordingly, in a first aspect of the present invention there is Provided a veterinary composition useful for treatment of energy depletion, dehydration and electrolyte imbalance in diarrhoeic neonatal animals consisting essentially of (a) glucose in an amount sufficient to produce a concentration level of from greater than 200 mM to 250 mM when in an aqueous solution,
(b) one or more sodium salts in an amount sufficient to produce a sodium ion concentration level of from 60 mM to 120 mM when in an aqueous solution, and
(c) one or more chloride salts in an amount sufficient to produce a chloride ion concentration level of 50 mM to 90 mM when in an aqueous solution.

In a further aspect of the present invention there is provided a veterinary composition useful for treatment of energy depletion, dehydration and electrolyte imbalance in diarrhoeic neonatal animals consisting essentially of (a) glucose in an amount sufficient to produce a concentration level of from greater than 200 mM to 250 mM when in an aqueous solution,
(b) one or more sodium salts in an amount sufficient to produce a sodium ion concentration level of from 60 mM to 120 mM when in an aqueous solution,
(c) one or more chloride salts in an amount sufficient to produce a chloride ion concentration level of 50 mM to 90 mM when in an aqueous solution, and
(d) one or more bicarbonate salts in an amount sufficient to produce a bicarbonate ion concentration level of 20 mM to 40 mM when in an aqueous solution.

The veterinary composition according to the present invention may be in oral dosage form.

The veterinary composition according to the present invention may be in solid or powder form. The veterinary composition according to the present invention may be in the form of a solution. An aqueous solution is preferred. Desirably the composition may be provided in a solid or powder form for transport. The end user may then form the composition into an aqueous solution.

The amount of glucose which may be included in the composition should provide sufficient energy for survival of scouring calves in all Prevailing weather conditions. The minimum energy requirement will vary. However at least 50% of the normal maintenance energy requirements of the neonatal calf should be provided.

Accordingly, a concentration level of greater than approximately 200 mM glucose in aqueous solution form is required taking into consideration the appetitie of neonatal calves. It will be understood that the concentration of glucose should be as high as possible to provide the calf with sufficient nutrition. However the level of glucose is limited as a complicating fermentative diarrhoea may occur if too great a level of glucose is used. Glucose concentrations of up to 250 mM may be safely used if sufficient sodium is also provided. The glucose concentration should not be beyond an upper limit of approximately 250 mM.

Glucose may be present in the form of anhydrous dextrose or dextrose monohydrate. In order to achieve the concentrations specified above, dextrose monohydrate may be present in the veterinary compositions in amounts of from approximately 39 gm to 50 gm per liter of the final aqueous solution.

The anhydrous dextrose may be present in amounts of from approximately 35 gm to 45 gm per litre of the final aqueous solution.

Sodium ($Na^+$) ions are included in the solution primarily to couple with glucose to draw water from the gut lumen into the body and secondly to replace increased sodium losses in diarrhoeic faeces. Sodium ions are thus very important in minimising dehydration, one of the principle effects of diarrhoea, and in maximizing glucose uptake thus preventing hypoglycemia and fermentative diarrhoea. A minimum concentration of 60 mM sodium is required for maximum glucose and water absorption from a 200-250 mM glucose solution. Faecal sodium ($Na^+$) losses in diarrhoeic calves are usually in the order of 40 mM although they may be as high as 89 to 137 mM. Accordingly, the concentration of sodium ions in the veterinary composition may vary from approximately 60 to 120 mM sodium ions.

Chloride ($Cl^-$) ions are also included in the solution to promote water absorption and to replace faecal losses. Chloride ion losses are understood in general to parallel those of sodium ions. It will be understood that full replacement of chloride ions is not considered essential. Chloride must be present as the major anion or maximum water absorption however part of the chloride ions replacement may be substituted by other anionic electrolytes as discussed below. Accordingly, a suitable range of chloride ion concentration in the veterinary composition according to the present invention may be from approximately 50 to 90 mM in aqueous solution form.

The preferred source of sodium ions and chloride ions is sodium chloride (NaCl). However other sources of such ions may be used.

Sodium chloride (NaCl) may be present in the veterinary compositions in amounts of from approximately 3.5 gm per liter to 5.2 gm per liter of the final aqueous solution.

As stated above, the veterinary composition according to the present invention may further include (a) glucose in an amount sufficient to produce a concentration level of from greater than 200 mM to 250 mM when in an aqueous solution, (b) one or more sodium salts in an amount sufficient to produce a sodium ion concentration level of from 60 mM to 120 mM when in an aqueous solution, (c) one or more chloride salts in an amount sufficient to produce a chloride ion concentration level of 50 mM to 90 mM when in an aqueous solution, and (d) one or more bicarbonate salts in an amount sufficient to produce a bicarbonate ion concentration level of 20 mM to 40 mM when in an aqueous solution.

Bicarbonate ions may be introduced into the composition as sodium bicarbonate ($NaHCO_3$). Bicarbonate ions may be of benefit to animals which are in an advanced state of acidosis when treatment has commenced. A composition containing 40 mM bicarbonate has been found to be useful in diarrhoeic calves without affecting palatability.

Bicarbonate ion as sodium bicarbonate ($NaCHO_3$) may be present in an amount of from approximately 1.7 gm to 3.4 gm per liter of the final aqueous solution.

As stated above, the veterinary composition according to the present invention may further include (a) glucose in an amount sufficient to produce a concentration level of from greater than 200 mM to 250 mM when in an aqueous solution, (b) one or more sodium salts in an amount sufficient to produce a sodium ion concentration level of from 60 mM to 120 mM when in an aqueous solution, (c) one or more chloride salts in an amount sufficient to produce a chloride ion concentration of 50 mM to 90 mM when in an aqueous solution, (d) one or more bicarbonate salts in an amount sufficient to produce a bicarbonate in concentration level of 20 to 40 mM when in an aqueous solution, and (e) one or more citrate salts in an amount sufficient to produce a citrate ion concentration level of 1 mM to 35 mM when in an aqueous solution.

Citrate ions may be included in the composition according to the present invention as they have a two-fold effect. Firstly they may be used Partially or completely in place of bicarbonate ions. Secondly they may be used at very low concentration levels in order to increase fluid uptake across the gut wall. Thus a concentration of approximately 1 to 35 mM of citrate ions may be included in an aqeuous solution of the veterinary composition according to the Present invention. However, the sum of bicarbonate and citrate concentrations should not exceed 40 mM so that chloride stimulated water absorption is not interfered with. The source of citrate ions may be sodium citrate.

In a particularly preferred form, the veterinary composition may include an aqueous solution of approximately 227 mM glucose, 86 mM sodium ($Na^+$) ions and 86 mM chloride ($Cl^-$) ions.

This is equivalent to approximately 45 gm/l glucose and 5 gm/l NaCl.

In a preferred form, the veterinary composition may comprise (a) approximately 88% w/w to approximately 94% w/w of glucose monohydrate based on the total weight of the veterinary composition, (b) approximately 6% w/w to approximately 12% w/w of sodium chloride based on the total weight of the veterinary composition.

In a further preferred form, the veterinary composition may comprise a veterinary composition comprising (a) approximately 83% w/w to approximately 92% w/w of dextrose (anhydrous) based on the total weight of the veterinary composition, (b) approximately 7% w/w to 10% w/w of sodium chloride based on the total weight of the veterinary composition, and (c) approximately 4% w/w to approximately 6.5% w/w of sodium bicarbonate based on the total weight of the veterinary composition.

In order to achieve the desired ion concentration the veterinary composition including dextrose monohydrate may be present in an aqueous solution in amounts of approximately 44.1 to 58.1 gm per liter. The veterinary composition including dextrose (anhydrous) may be present in amounts of approximately 40.5 to 53.6 gm per liter.

In a preferred aspect of the present invention there is provided a veterinary composition useful for treatment of energy depletion, dehydration and electrolyte imbalance in diarrhoeic neonatal animals consisting essentially of (a) glucose in an amount sufficient to produce a concentration level of from greater than 200 mM to 250 mM when in an aqueous solution, (b) one or more sodium salts in an amount sufficient to produce a sodium ion concentration level of from 60 mM to 120 mM when in an aqueous solution, (c) one or more chloride salts in an amount sufficient to produce a chloride ion concentration of 50 mM to 90 mM when in an aqueous solution, (d) one or more bicarbonate salts in an amount sufficient to produce a bicarbonate in concentration level of 20 to 40 mM when in an aqueous solution, and (e) one or more citrate salts in an amount sufficient to produce a citrate ion concentration level of 1 mM to 35 mM when in an aqueous solution.

In a further preferred aspect there is provided a mixture consisting essentially of a veterinary composition useful for treatment of energy depletion, dehydration and electrolyte imbalance in diarrhoeic neonatal animals consisting essentially of
(a) glucose in an amount sufficient to produce a concentration level of from greater than 200 mM to 250 mM when in an aqueous solution,
(b) one or more sodium salts in an amount sufficient to produce a sodium ion concentration level of from 60 mM to 120 mM when in an aqueous solution, and
(c) one or more chloride salts in an amount sufficient to produce a chloride ion concentration level of 50 mM to 90 mM when in an aqueous solution, and
milk or a milk product in an approximately 1:1 volume to volume mixture.

In accordance with a further aspect of the present invention there is provided a method for the treatment of animal diarrhoea which comprises administering to a neonatal animal requiring such treatment an antidiarrheal amount of a veterinary composition useful for treatment of energy depletion, dehydration and electrolyte imbalance in diarrhoeic animals consisting essentially of an aqueous solution of
(a) glucose in an amount sufficient to produce a concentration level of from 200 mM to 250 mM when in an aqueous solution,
(b) one or more sodium salts in an amount sufficient to produce a sodium ion concentration level of from 60 mM to 120 mM when in an aqueous solution, and
(c) one or more chloride salts in an amount sufficient to produce a chloride ion concentration level of 50 mM to 90 mM when in an aqueous solution.

The veterinary composition may be in the form of an aqueous solution for oral administration.

The veterinary composition may be administered twice daily. The veterinary composition may be administered in amounts of approximately 1.5 to 2 liters depending on the size of the calf, (smaller amounts would be suitable for piglets). The treatment may continue for two days during which milk should not be fed. The veterinary composition may then be administered as a mixture of composition and milk. The mixture may be an approximately 1:1 volume/volume mixture.

For example, approximately 0.75 liters of solution may be mixed with approximately 0.75 liters of milk and administered to the animal twice daily for two days.

Preferably the veterinary composition is administered in amounts of 3 to 4 liters per day for two to three days.

More preferably, the veterinary composition is administered for two days and after the second day of treatment the veterinary composition is administered as an approximate 1:1 volume/volume mixture of the composition and milk.

Alternatively the veterinary composition may be administered on alternate feedings to an approximately equivalent volume of milk.

The invention will now be more fully described with reference to the accompanying example. It should be understood however, that this example is illustrative and should not be taken in any way as a restriction on the generality of the invention described above.

EXAMPLE 1
PROPORTIONS OF INGREDIENTS
A - Using dextrose monohydrate; no sodium bicarbonate

| Ingredient | mM | g/liter solution | g/kg powder | Comment |
|---|---|---|---|---|
| (i) Max glucose, min NaCl | | | | |
| Dextrose M.H. | 250 | 49.5 | *934 | Min NaCl limited |
| NaCl | 60 + 60 | 3.5 | *66 | by min Na+ |
| Total | 370 | 54.0 | 1000 | conc. |
| (ii) Min glucose, max NaCl | | | | |
| Dextrose M.H. | 200 | 39.6 | *884 | Max NaCl limited |
| NaCl | 90 + 90 | 5.2 | *116 | by max Cl− |
| Total | 380 | 44.8 | 1000 | conc. |
| (iii) Max Powder mixture/liter | | | | |
| Dextrose M.H. | 250 | 49.5 | | |
| NaCl | 90 + 90 | 5.2 | | |
| Total | 430 | *54.7 g/l | | |
| (iv) Min Powder mixture/liter | | | | |
| Dextrose M.H. | 200 | 39.6 | | |
| NaCl | 60 + 60 | 3.5 | | |
| Total | 320 | *43.1 g/l | | |

B - Using dextrose monohydrate and sodium bicarbonate

| Ingredient | mM | g/liter solution | g/kg powder | Comment |
|---|---|---|---|---|
| (i) Max glucose | | | | |
| Dextrose M.H. | 250 | 49.5 | *915 | |
| NaCl | 50 + 50 | 2.9 | 54 | |
| NaHCO3 | 20 + 20 | 1.7 | 31 | |
| Total | 390 | 54.1 | 1000 | |
| (ii) Min glucose | | | | |
| Dextrose M.H. | 200 | 39.6 | *832 | Amt. NaCl limited |
| NaCl | 80 + 80 | 4.6 | 97 | by max Na+ (120 mM) |
| NaHCO3 | 40 + 40 | 3.4 | 71 | |
| Total | 440 | 47.6 | 1000 | |
| (iii) Max NaCl | | | | |
| Dextrose M.H. | 200 | 39.6 | 822 | |
| NaCl | 90 + 90 | 5.2 | *108 | |
| NaHCO3 | 40 + 40 | 3.4 | 70 | |
| Total | 460 | 48.2 | 1000 | |
| (iv) Min NaCl | | | | |
| Dextrose M.H. | 250 | 49.5 | 887 | |
| NaCl | 50 + 50 | 2.9 | *52 | |
| NaHCO3 | 40 + 40 | 3.4 | 61 | |
| Total | 430 | 55.8 | 1000 | |
| (v) Max NaHCO3 | | | | |
| Dextrose M.H. | 200 | 39.6 | 863 | |
| NaCl | 50 + 50 | 2.9 | 63 | |
| NaHCO3 | 40 + 40 | 3.4 | *74 | |
| Total | 420 | 45.9 | 1000 | |
| (vi) Min NaHCO3 | | | | |
| Dextrose M.H. | 250 | 49.5 | 878 | |
| NaCl | 90 + 90 | 5.2 | 92 | |
| NaHCO3 | 20 + 20 | 1.7 | *30 | |
| Total | 470 | 56.4 | 1000 | |
| (vii) Max powder mixt./liter soln. | 250 | 49.5 | | Amount of NaCl limited by max Na+ conc. (120 mM) |
| Dextrose M.H. | | | | |
| NaCl | 80 + 80 | 4.6 | | |
| NaHCO3 | 40 + 40 | 3.4 | | |

B - Using dextrose monohydrate and sodium bicarbonate

| Ingredient | mM | g/liter solution | g/kg powder | Comment |
|---|---|---|---|---|
| Total | 490 | *57.5 g/l | | |
| (viii) Min powder mixt./liter soln. | | | | |
| Dextrose M.H. | 200 | 39.6 | | |
| NaCl | 50 + 50 | 2.9 | | |
| NaHCO3 | 20 + 20 | 1.7 | | |
| Total | 340 | *44.2 g/l | | |

C - Using anhydrous dextrose; no sodium bicarbonate

| Ingredient | mM | g/liter solution | g/kg powder |
|---|---|---|---|
| (i) Max glucose, min NaCl | | | |
| Anh. dextrose | 250 | 45.0 | *928 |
| NaCl | 60 + 60 | 3.5 | *72 |
| Total | 370 | 48.5 | 1000 |
| (ii) Min glucose, max NaCl | | | |
| Anh. dextrose | 200 | 36.0 | *874 |
| NaCl | 90 + 90 | 5.2 | *126 |
| Total | 380 | 41.2 | 1000 |
| (iii) Max Powder mixt./liter | | | |
| Anh. dextrose | 250 | 45.0 | |
| NaCl | 90 + 90 | 5.2 | |
| Total | 430 | *50.2 g/l | |
| (iv) Min Powder mixt./liter | | | |
| Anh. dextrose | 200 | 36.0 | |
| NaCl | 60 + 60 | 3.5 | |
| Total | 320 | *39.5 g/l | |

D - Using anhydrous dextrose and sodium bicarbonate

| Ingredient | mM | g/liter solution | g/kg powder | Comment |
|---|---|---|---|---|
| (i) Max glucose | | | | |
| Dextrose anh. | 250 | 45.0 | *907 | |
| NaCl | 50 + 50 | 2.9 | 59 | |
| NaHCO3 | 20 + 20 | 1.7 | 34 | |
| Total | 390 | 49.6 | 1000 | |
| (ii) Min glucose | | | | |
| Dextrose anh. | 200 | 36.0 | *818 | |
| NaCl | 80 + 80 | 4.6 | 105 | |
| NaHCO3 | 40 + 40 | 3.4 | 77 | |
| Total | 440 | 44.0 | 1000 | |
| (iii) Max NaCl | | | | |
| Dextrose anh. | 200 | 36.0 | 807 | |
| NaCl | 90 + 90 | 5.2 | *117 | |
| NaHCO3 | 40 + 40 | 3.4 | 76 | |
| Total | 460 | 44.6 | 1000 | |
| (iv) Min NaCl | | | | |
| Dextrose anh. | 250 | 45.0 | 877 | |
| NaCl | 50 + 50 | 2.9 | *57 | |
| NaHCO3 | 40 + 40 | 3.4 | 66 | |
| Total | 430 | 51.3 | 1000 | |
| (v) Max NaHCO3 | | | | |
| Dextrose anh. | 200 | 36.0 | 851 | |
| NaCl | 50 + 50 | 2.9 | 69 | |
| NaHCO3 | 40 + 40 | 3.4 | *80 | |
| Total | 420 | 42.3 | 1000 | |
| (vi) Min NaHCO3 | | | | |
| Dextrose anh. | 250 | 45.0 | 867 | |
| NaCl | 90 + 90 | 5.2 | 100 | |
| NaHCO3 | 20 + 20 | 1.7 | *33 | |
| Total | 470 | 51.9 | 1000 | |
| (vii) Max Powder mixt./liter soln. | | | | |
| Anh. Dextrose | 250 | 45.0 | | |
| NaCl | 80 + 80 | 4.6 | | |
| NaHCO3 | 40 + 40 | 3.4 | | |
| Total | 490 | *53.0 g/l | | |
| (viii) Min Powder mixt./liter soln. | | | | |
| Anh. Dextrose | 200 | 36.0 | | |
| NaCl | 50 + 50 | 2.9 | | |
| NaHCO3 | 20 + 20 | 1.7 | | |
| Total | 340 | *40.6 g/l | | |

1 Kg of the veterinary compositions A, B, C, D, were prepared by mixing together the ingredients in dry powder form.

EXAMPLE 2

A veterinary composition according to the present invention in the form of an aqueous solution containing 227 mM glucose, 86 mM Na+ and 86 mM Cl− was fed to calves which became diarrhoeic following infection with rotavirus and cryptosporidia.

Other calves were fed with electrolyte only or electrolyte glycine, glucose mixtures having compositions as set out in FIG. 1. Diarrhoeic calves (12) were deprived of milk and fed 1.5 liters of the solution alone twice daily for 2 days, then fed 0.75 liters of the solution with 0.75 liters milk twice daily for 2 days. Calves treated with the solution became significantly less acidotic ($P<0.02$ days 2–4) and less dehydrated ($P<0.05$ days 1–3) than control diarrhoeic calves (12) fed 1.5 liters milk twice daily.

Figure 3:
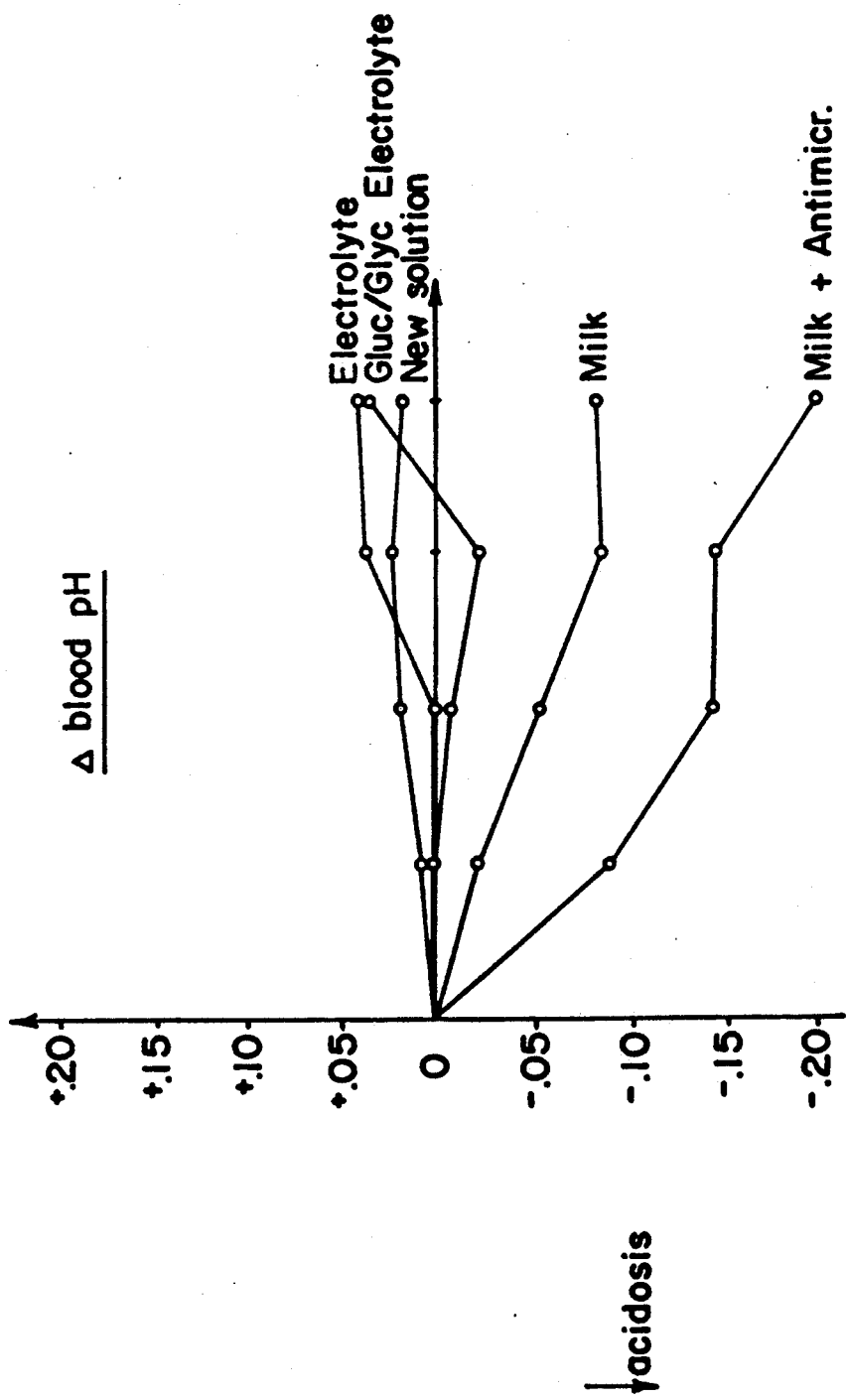

The effects of such treatments on acidosis and dehydration of calves are set out in FIGS. 2 and 3. FIG. 4 also shows the number of calves in each group found to be moribund. From a review of these Figures it will be noted that diarrhoeic calves fed a commercial electrolyte-only solution or a commercial solution containing glucose (125 mM), glycine and electrolytes also became significantly less acidotic and dehydrated than milk fed controls. However some calves in both these treatment groups became severely hypoglycaemic and moribund. Diarrhoeic calves continued on milk and given an oral antimicrobial became significantly more acidotic ($P<0.05$ days 1.2) than diarrhoeic control calves fed milk alone.

In the trials calves were allotted to treatment groups with consideration to immunoglobulin status, bodyweight, initial severity of diarrhoea and initial degree of acidosis and dehydration. Under these circumstances the new veterinary composition according to the present invention was effective in minimizing acidosis, dehydration and hypoglycaemia in calves infected with rotavirus and cryptosporidia. None of the calves died in the new solution treatment group during the experiments but calves died with severe hypoglycaemia in the two other milk deprived treatment groups (FIG. 4). Although the number of deaths are too small for significance data, blood changes in the milk-deprived moribund calves indicate the glucose/energy content of currently available solutions is too low.

EXAMPLE 3

A further trial was conducted at the Regional Veterinary Laboratory Bairnsdale, Victoria to compare glucose and fluid absorption from a high glucose electrolyte solution according to the present invention with that obtained from a composition according to Bywater U.S. Pat. No. 4,164,568 that has a lower glucose concentration.

Glucose absorption was monitored by blood glucose concentration and fluid absorption was monitored by change in blood packed cell volume and plasma protein concentration. Preliminary statistical analysis has been performed using the T-test for comparison of means of 2 groups.

To conduct the trial treatment compositions were prepared in 1 kg quantities by hand using laboratory grade chemicals and laboratory balances. For the composition according to the present invention, designated the Jerrett composition, 1 kg of treatment powder was prepared by mixing 880 g glucose monohydrate, 70 g of sodium chloride and 50 g of sodium bicarbonate. For the composition according to the Bywater U.S. Pat., designated the Beecham composition, 1 kg of treatment powder was prepared by mixing 720 g glucose monohydrate, 135 g sodium chloride, 25 g potassium chloride, 100 g glycine, and 20 g trisodium citrate.

Table 1 issustrates the compositions fed to the groups of calves used in the trial. In this trial health dairy claves 4-5 weeks old were allocated to 2 groups of 8 and each group was fed one of the compositions in Table 1. The dry compositions were added to water at a rate of 50 g/l and fed at a rate of 55 ml solution per kg bodyweight. The concentration of the solutions were confirmed by colorimetry (glucose) and flame photometry (sodium).

TABLE 1

| Trial 1 Dry Compositions | | |
|---|---|---|
| | JERRETT | BEECHAM |
| Glucose monohydrate | 88% | 72% |
| Sodium chloride | 7% | 13.5% |
| Sodium bicarbonate | 5% | — |
| Potassium chloride | | 2.5% |
| Glycine | | 10% |
| Trisodium citrate | | 2% |
| Solutions made by dissolving 50 g of dry composition per liter of water. | | |
| Osmolarity | 402 mM | 527 mM |
| Glucose | 222 mM | 182 mM |
| Sodium | 90 mM | 125 mM |
| Chloride | 60 mM | 133 mM |
| Bicarbonate | 30 mM | — |
| Potassium | | 17 mM |
| Citrate | | 3 mM |
| Glycine | | 67 mM |

To analyse the effectivenss of the treatment compositions blood samples were collected from calves into evacuated tubes containing either lithium heparin or sodium fluoride/potassium oxalate anticoagulants. Packed cell volumes were determined on lithium heparin blood samples using standard microhaematocrit techniques. Protein assays were performed on lithium hiparin blood plasma and glucose assays were performed on sodium fluoride/potassium oxadate blood plasma by clorimetric methods using commercial kits (Boeringer) on a Roche Cobas Mira autoanalyser. Protein was measured by the Biuret method and glucose was measured by the GOD-Perid method.

Figure 5:
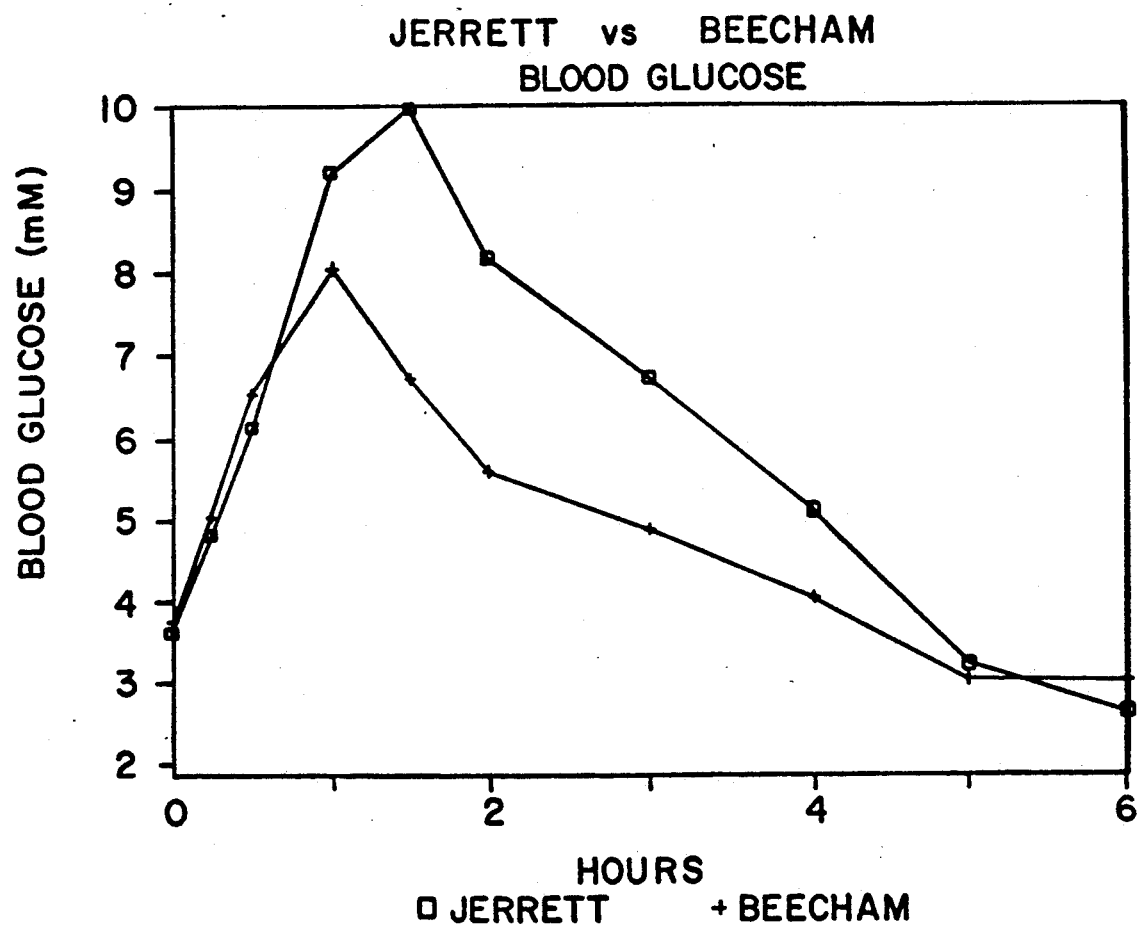

FIG. 5 illustrates the glucose absorption in the blood of the groups of calves used in the experiment as measured against time. From this information it can be seen that glucose absorption was significantly higher from the solution according to the present invention as demonstrated by mean blood gluocse levels ($p < 0.02$ 1.5–2 hours, $p < 0.05$ 3 hours) following feeding. The difference in glucose absorptions two hours after administration was 50% whereas the different in glucose concentration in the formulations was only 22%. Thus the increase is much greater than might have been predicted from the compositions. Moreover, veterinarians have traditionally believed that any increase in blood glucose would be less than the 22% as animal bodies are not capable of higher absorption of glucose.

Figure 6:
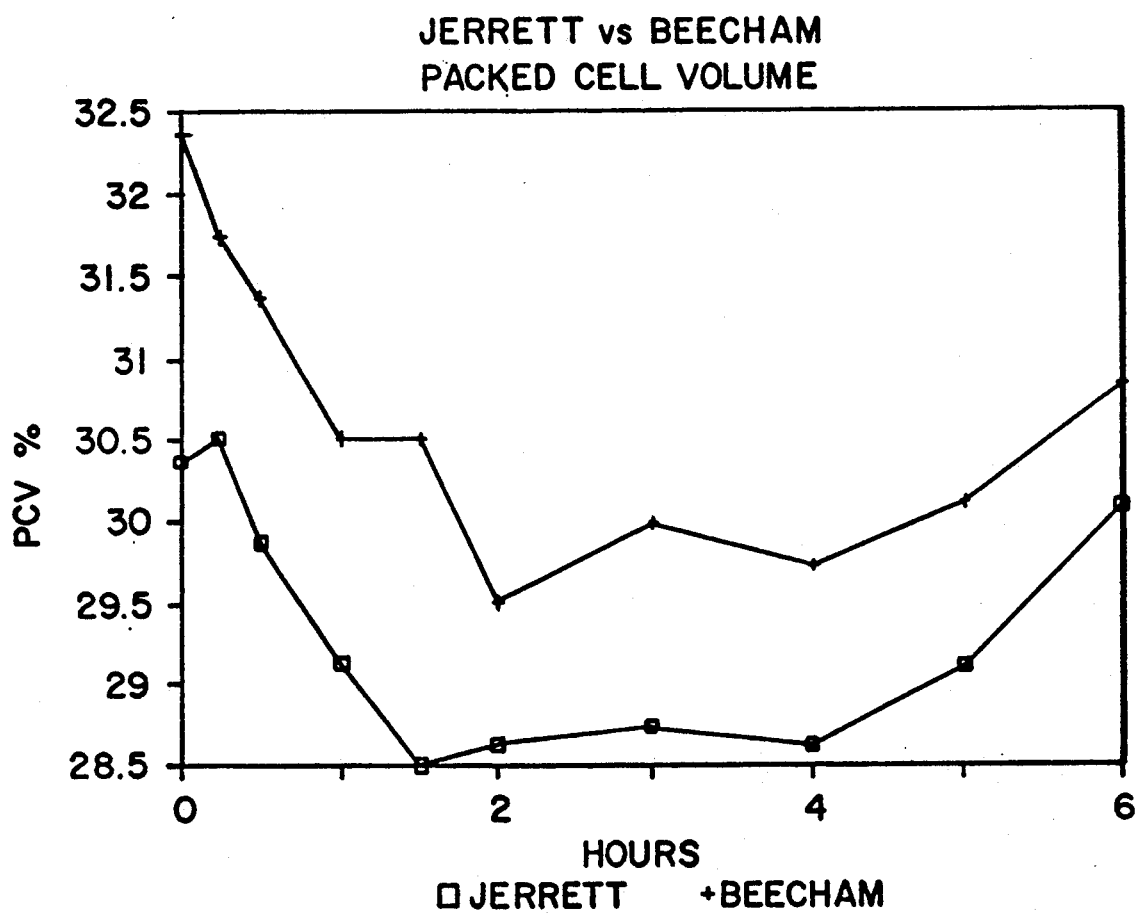
Figure 7:
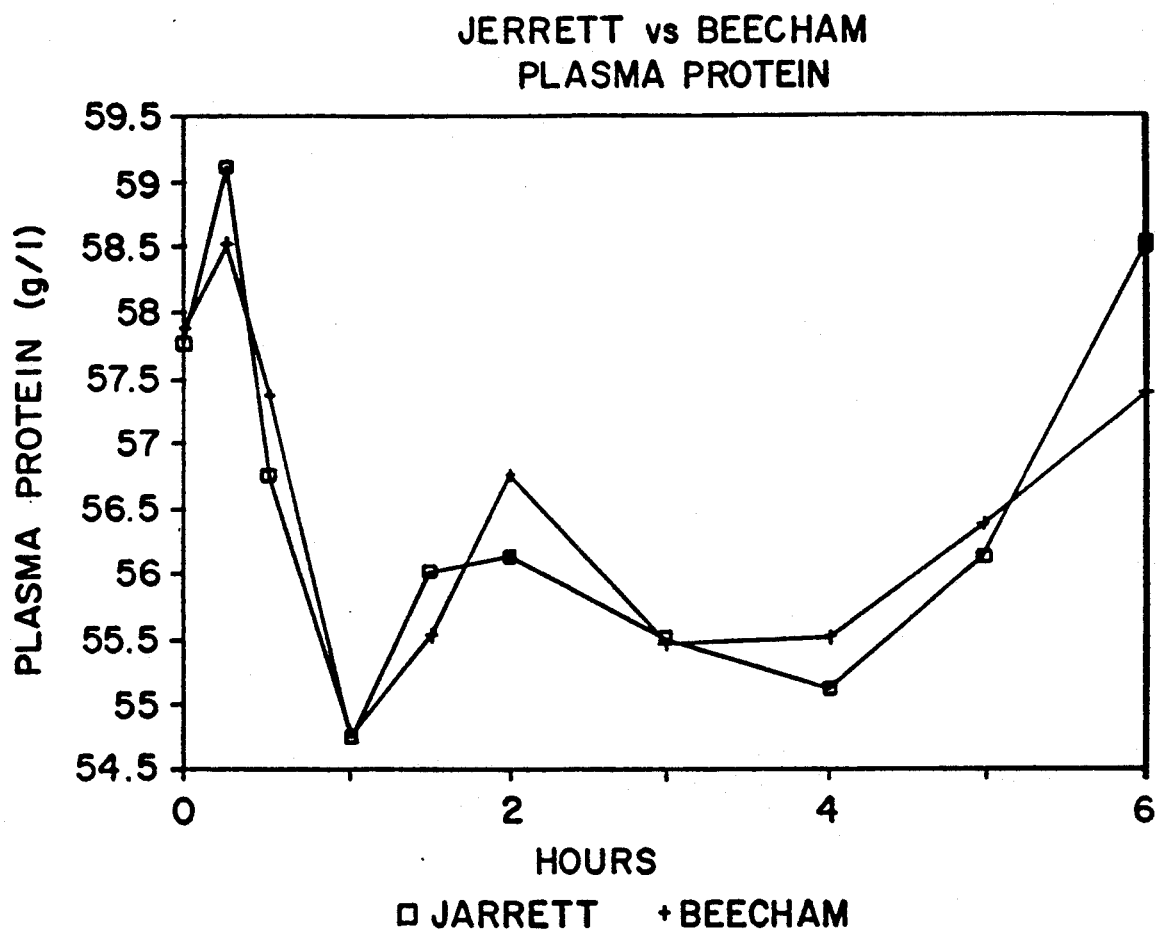

FIGS. 6 and 7 illustrate the fluid absorption, as measured by change in PCV and plasma protein. These figures establish that the fluid absorption was not significantly difference between the groups. This is the desired result. This trial demonstrates the clear advantage of the present formulation by providing significantly higher glucose absorption and a consequent energy repletion whilst maintaining the fluid absorption characteristics for which oral glucose-electrolyte solutions were originally developed.

Finally, it is to be understood that various other modifications and/or alterations may be made without departing from the spirit of the present invention as outlined herein.

I claim:

1. A veterinary composition useful for treatment of energy depletion, dehydration and electrolyte imbalance in diarrhoeic neonatal animals consisting essentially of
   (a) glucose in an amount sufficient to produce a concentration level of from greater than 200 mM to 250 mM when in an aqueous solution,
   (b) one or more sodium salts in an amount sufficient to produce a sodium ion concentration level of from 60 mM to 120 mM when in an aqueous solution, and
   (c) one or more chloride salts in an amount sufficient to produce a chloride ion concentration level of 50 mM to 90 mM when in an aqueous solution.

2. The veterinary composition of claim 1 consisting essentially of
   (a) 88% w/w to 94% w/w of glucose monohydrate based on the total weight of the veterinary composition
   (b) approximately 6% w/w to approximately 12% w/w of sodium chloride based on the total weight of the veterinary composition.

3. A veterinary composition useful for treatment of energy depletion, dehydration and electrolyte imbalance in diarrhoeic neonatal animals consisting essentially of
   (a) glucose in an amount sufficient to produce a concentration level of from greater than 200 mM to 250 mM when in an aqueous solution,
   (b) one or more sodium salts in an amount sufficient to produce a sodium ion concentration level of from 60 mM to 120 mM when in an aqueous solution,
   (c) one or more chloride salts in an amount sufficient to produce a chloride ion concentration level of 50 mM to 90 mM when in an aqueous solution, and (d) one or more bicarbonate salts in an amount sufficient to produce a bicarbonate ion concentration level of 20 mM to 40 mM when in an aqueous solution.

4. The veterinary composition of claim 3 consisting essentially of
(a) 83% w/w to 92% w/w of glucose monohydrate based on the total weight of the veterinary composition
(b) approximately 5% w/w to 11% w/w of sodium chloride based on the total weight of the veterinary composition, and
(c) 3% to 8% w/w of sodium bicarbonate based on the total weight of the veterinary composition.

5. The veterinary composition of claim 1 consisting essentially of
(a) 87% w/w to 93% w/w of dextrose (anhydrous) based on the total weight of the veterinary composition,
(b) 7% w/w to 13% w/w of sodium chloride based on the total weight of the veterinary composition.

6. The veterinary composition consisting essentially of
(a) 81% w/w to 91% w/w of dextrose (anhydrous) based on the total weight of the veterinary composition,
(b) 5% w/w to 12% w/w of sodium chloride based on the total weight of the veterinary composition,
(c) 3% w/w to 8% w/w of sodium bicarbonate based on the total weight of the veterinary composition.

7. The veterinary composition according to any one of claims 1 to 6 in an aqueous solution.

8. A method for the treatment of animal diarrhoea which comprises administering to a neonatal animal requiring such treatment an antidiarrheal amount of a veterinary composition useful for treatment of energy depletion, dehydration and electrolyte imbalance in diarrhoeic animals consisting essentially of an aqueous solution of
(a) glucose in an amount sufficient to produce a concentration level of from 200 mM to 250 mM when in an aqueous solution,
(b) one or more sodium salts in an amount sufficient to produce a sodium ion concentration level of from 60 mM to 120 mM when in an aqueous solution, and
(c) one or more chloride salts in an amount sufficient to produce a chloride ion concentration level of 50 mM to 90 mM when in an aqueous solution.

9. The method according to claim 8 wherein the neonatal animal is a neonatal calf or piglet.

10. The method according to claim 8, wherein the antidiarrheal amount administered is 3 to 4 liters per day for two to three days.

11. The method according to claim 10 wherein the veterinary composition is administered for two days and after the second day of treatment the veterinary composition is administered as an approximate 1:1 volume/volume mixture of the composition and milk.

12. A veterinary composition useful for treatment of energy depletion, dehydration and electrolyte imbalance in diarrhoeic neonatal animals consisting essentially of
(a) glucose in an amount sufficient to produce a concentration level of from greater than 200 mM to 250 mM when in an aqueous solution,
(b) one or more sodium salts in an amount sufficient to produce a sodium ion concentration level of from 60 mM to 120 mM when in an aqueous solution,
(c) one or more chloride salts in an amount sufficient to produce a chloride ion concentration of 50 mM to 90 mM when in an aqueous solution,
(d) one or more bicarbonate salts in an amount sufficient to produce a bicarbonate in concentration level of 20 to 40 mM when in an aqueous solution, and
(e) one or more citrate salts in an amount sufficient to produce a citrate ion concentration level of 1 mM to 35 mM when in an aqueous solution.

13. A mixture consisting essentially of a veterinary composition useful for treatment of energy depletion, dehydration and electrolyte imbalance in diarrhoeic neonatal animals consisting essentially of
(a) glucose in an amount sufficient to produce a concentration level of from greater than 200 mM to 250 mM when in an aqueous solution,
(b) one or more sodium salts in an amount sufficient to produce a sodium ion concentration level of from 60 mM to 120 mM when in an aqueous solution, and
(c) one or more chloride salts in an amount sufficient to produce a chloride ion concentration level of 50 mM to 90 mM when in an aqueous solution, and
milk or a milk product in an approximately 1:1 volume to volume mixture.

14. A mixture consisting essentially of a veterinary composition useful for treatment of energy depletion, dehydration and electrolyte imbalance in diarrhoeic neonatal animals consisting essentially of
(a) glucose in an amount sufficient to produce a concentration level of from greater than 200 mM to 250 mM when in an aqueous solution,
(b) one or more sodium salts in an amount sufficient to produce a sodium ion concentration level of from 60 mM to 120 mM when in an aqueous solution,
(c) one or more chloride salts in an amount sufficient to produce a chloride ion concentration level of 50 mM to 90 mM when in an aqueous solution, and
(d) one or more bicarbonate salts in an amount sufficient to produce a bicarbonate ion concentration level of 20 mM to 40 mM when in an aqueous solution, and
milk or a milk product in an approximately 1:1 volume to volume mixture.

15. A mixture consisting essentially of a veterinary composition useful for treatment of energy depletion, dehydration and electrolyte imbalance in diarrhoeic neonatal animals consisting essentially of
(a) glucose in an amount sufficient to produce a concentration level of from greater than 200 mM to 250 mM when in an aqueous solution,
(b) one or more sodium salts in an amount sufficient to produce a sodium ion concentration level of from 60 mM to 120 mM when in an aqueous solution,
(c) one or more chloride salts in an amount sufficient to produce a chloride ion concentration of 50 mM to 90 mM when in an aqueous solution,
(d) one or more bicarbonate salts in an amount sufficient to produce a bicarbonate ion concentration level of 20 mM to 40 mM when in an aqueous solution, and
(e) one or more citrate salts in an amount sufficient to produce a citrate ion concentration level of 1 mM to 35 mM when in an aueous solution, and
milk or a milk product in an roximately 1:1 volume to volume mixture.

* * * * *